United States Patent [19]

Kobayashi et al.

[11] 3,972,993

[45] Aug. 3, 1976

[54] INSECTICIDAL DEVICE

[75] Inventors: Hidetoshi Kobayashi; Yoshiaki Niitani; Hilomithu Abiru, all of Iwaki, Japan

[73] Assignee: Kureha Kagaku Kogyo Kabushiki Kaisha, Tokyo, Japan

[22] Filed: Nov. 7, 1974

[21] Appl. No.: 521,919

[30] Foreign Application Priority Data
Nov. 13, 1973  Japan............................... 48-126769

[52] U.S. Cl. .................................... 424/15; 43/124; 43/131; 424/17; 424/84
[51] Int. Cl.² ....................... A01N 9/00; A01M 1/00
[58] Field of Search ................ 43/131, 124; 424/15, 424/17, 84

[56] References Cited
UNITED STATES PATENTS

| | | | |
|---|---|---|---|
| 2,893,160 | 7/1959 | Grant | 43/131 |
| 3,173,223 | 3/1965 | Dunn et al. | 43/131 |
| 3,304,646 | 2/1967 | Staley | 43/131 |
| 3,324,590 | 6/1967 | Richardson | 43/131 |

Primary Examiner—Shep K. Rose
Attorney, Agent, or Firm—Holman & Stern

[57] ABSTRACT

An insecticidal device includes a core of an insect-attracting substance. The core is substantially covered with at least one perforated cover sheet covering at least part of the surface of the core, the cover sheet being coated on its exposed outer surface with a insecticidal agent. The perforations in the cover sheet have dimensions such that an insect trying to reach the insect-attracting substance will necessarily contact the insecticidal agent on the exposed outer surface of the cover sheet.

1 Claim, 1 Drawing Figure

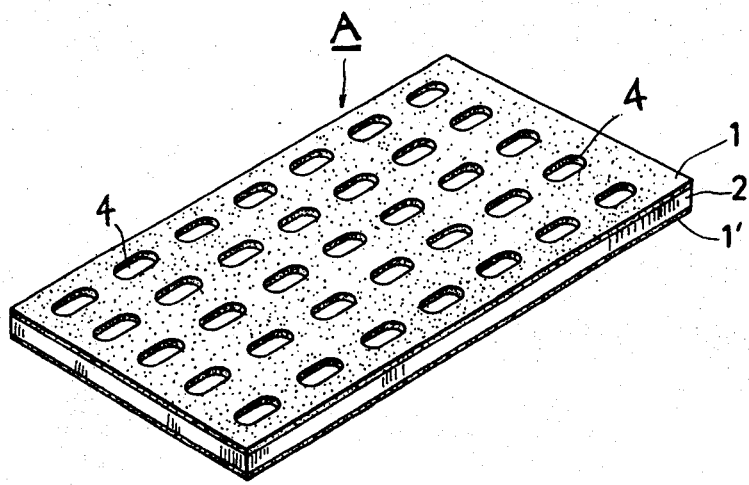

INSECTICIDAL DEVICE

BACKGROUND OF THE INVENTION

This invention relates to a device adapted for attracting and killing insects.

In the past, various and numerous insect-attracting and killing agents have been proposed. However, it should be noted that such agents are generally characterized by the combination of an insect-attracting agent with an insecticidal chemical. As an example, an insect-attracting agent and insect-killer are combined and shaped, so as to provide a device adapted for these purposes. As an alternative measure, paper or the like shaped material is coated or impregnated with an attracting substance in combination with an insecticide and, in practical use, the shaped composition is contacted with water, thereby energizing its attracting activity. Such devices are now broadly commercialized.

Frequently, however, troubles have been encountered by the decomposition of the insect-killing chemical by contact with the attracting agent or with the water, thereby substantially reducing the otherwise expected long-extended, durable life of the residual effectiveness of the device. Under extreme conditions, and depending upon the kind and nature of the insecticide included in the device, the latter may become effectively useless by the loss of killing power.

The possible combinations of the insecticide with the attracting substance(s) are further subjected to a substantial limitation from the view point of uncertainty in the stability of the insecticide, thereby presenting a grave difficulty in the production of effective insect-attracting devices with satisfactory killing performance. When a mixture of the insect-killing chemical with attracting substance(s) which is applied on or to shaped carrier bodies is used, an appreciably excess amount of the insecticide must be consumed to keep the surface concentration thereof substantially at a predetermined constant concentration. This results unavoidably in a loss of economy.

SUMMARY OF THE INVENTION

While considering the various conventional drawbacks, an object of the present invention is to provide an improved insecticidal device wherein the insecticide cannot be adversely affected by the presence of insect-attracting agents.

A further object is to provide an improved insecticidal device of the above kind which is highly superior in its insectattracting and killing performances.

The basic principle of the present invention resides in that the structure of the basic carrier body is selected so that the attracting substance(s) and the insecticide are positioned independently from each other on the surface of said body and so that when insects land to eat the former substances, they must necessarily contact the latter agent. In this way, harmful insects and the like can be effectively killed.

These and further objects, and some of the features and advantages of the invention will become more apparent from the following detailed description of the invention when read in conjunction with the drawing which is illustrative of a preferred, representative embodiment of the invention.

BRIEF DESCRIPTION OF THE DRAWING

The sole FIGURE is a perspective view of one representative embodiment of the insecticidal device according to the invention.

DETAILED DESCRIPTION OF THE INVENTION

In the drawing, numerals 1 and 1' represent a pair of perforated sheets having a number of perforations 4. Although these perforations 4 are visible only on the upper perforated sheet 1, similar perforations are also provided through the material of the lower sheet. These perforations 4 are shown in the form of elongated and rounded openings as a representative example, but they may have a truly circular, square, flower-like or other decorative configuration, especially if a design and ornamental effect is desired, although this is not shown.

As an example, each of these elongated perforations 4 may have a length of 25mm and a width of approximately 6mm when the insects to be killed are house flies. The distance between these perforations 4 may amount to 2.5mm or so. The upper surface of the upper perforated sheet 1 is coated with an insecticidal agent to be described. The rate or percentage of the perforated area may amount to about 25–70%. The lower sheet 1' is coated on the exposed lower surface with the insecticidal agent.

A base sheet 2 is fixedly sandwiched between said perforated sheets 1 and 1'. This base sheet 2 may be made of one or more insect-attracting substance(s) selected for the particular insects to be killed. The thickness of the base sheet may be, if necessary, reduced to that of a thin film. Or alternatively, the thickness can be increased to provide a board. The selection may be determined as demanded by the circumstances. If necessary, the material of the base sheet 2 may be a previous one, so as to allow it to be impregnated with a liquid substance having the desired insectattracting effect(s). Under some circumstances, the base sheet 2 may be coated on one or both surfaces thereof with the substance(s) of the above kind.

The thus treated and assembled device generally denoted with "A" in the drawing, may have most preferably a rectangular board-like configuration as shown and can be used in a suspended state from the ceiling of a house.

If necessary, one of the perforated sheets 1 and 1' may be dispensed with, when the intention is to use the device on the floor or wall structure.

Although the device "A" has been shown representatively to have a rectangular plan configuration, the shape can be modified into a circle, ellipse, a flower-like or other decorative mode. The spatial configuration may also be modified from the board- or sheet shape, as may be demanded by the circumstances. An outer frame may be attached to the device when necessary for the purpose of safety and ornamental effects, although this is not shown.

The size of each of the perforations 4 should be such that house flies or the like harmful flies will necessarily contact the insecticidal agent on the exposed outer surface of the perforated sheet or sheets when they land on the device to eat the attracting agent(s). Therefore, the dimensions of the perforation 4 should not be too large or too small. In this respect, the selection of said opening dimensions 6mm × 25mm is only a representative measure. It should be determined by consideration of the dimensions of the fly or insect desired to be killed. Synthetic resin, rubber, paper, cloth or the like may be used for the material of the perforated sheets 1 and 1'.

When the employed material for the perforated sheets 1 and 1' shows a certain degree of penetration of the killer substance(s) towards the insect-attracting substance(s), a non-pervious and separating layer should be employed between each of the perforated sheets and the base sheet, preferably made of synthetic resin, rubber or the like.

The insect-killing substance should have the capacity of killing the insects, such as flies, by contact. Representatives thereof are, as an example, a complex salt of 0-methyl-0-(2,2-dichlorovinyl) calcium phosphate with 0,0-dimethyl-0-(2,2-dichlorovinyl) phosphate (abbreviated as CAVP hereinafter); DDVP; Diptelex (trade name by Bayer A.G., - 0,0-dimethyl-2,2,2-trichloro-1-hydroxyethyl phosphonate); Diazinone (trade name by Ciba-Geigy - 0,0-diethyl- 0-(2-isopropyl-4-methyl-6-pyrimidinyl phosphate); Bitex (trade name by Bayer A.G., - 0,0-dimehtyl-0-[(4-(methylthio)-m-tryl]phosphorothioate); "phenitrotion" and the like. These killing agents should have the least possible repelling characteristics.

The application of the insect-killin agent(s) onto the exposed surface of the perforated sheet 1 or 1' may be carried out by coating, spraying or the like conventional measure. In order to attain a strong fixture of the insecticide on the exposed surface of the perforated sheet 1 or 1', conventional fixing agents may be added. The amount of the applied insecticides may naturally vary depending upon the kinds of the killer and the insect. With CAVP, it is generally sufficient to use an amount of 0.1–10mg/cm$^2$.

The insect-attracting substance or substances may be used per se, or in combination with a conventional diluent and/or adhesive, and upon being shaped when necessary. Or alternatively, they may be used through impregnation in paper, sponge rubber or a foamed mass, having a porous, spongy or absorbing structure. Coating technique may also be utilized.

As the insect-attracting substance(s), sugar substances; finely divided or pasted corn and stern substaces; extracts; amino acids; amino acid derivatives; acetic acid derivatives; fatty acids; fatty acid derivatives and the like may be used.

The following several Examples are given for better understanding of the invention.

EXAMPLE 1

A rectangular sheet, with dimensions of 16cm × 6cm × 0.4mm, the latter being the thickness, made of a resin mixture of PVC and MBS, was perforated with 42 elongated perforations, each having a length of 24mm and a width of 6mm, with rounded ends, the ratio or percentage of open area amounting to about 54 percent. These perforations were evenly distributed in a geometrical manner, substantially as shown on the drawing. In this way, a pair of perforated sheets were provided. 175mg of CAVP per sheet were dissolved in acetone and coated on the exposed surface of the sheet, and dried to remove the solvent.

As the core sheet, two sheets of filter paper were combined together, and dipped into a solution of 8g of sugar in fresh water and dried.

The core sheet combination thus treated was combined with said two perforated sheets, in the similar way to that shown on the drawing. The resulting device was used for catching and killing flies in a house.

EXAMPLE 2

Two sheets of PVC-resin, each being 16cm × 6cm × 0.4mm, were evenly punched with 196 circular openings per sheet, the ratio of opening area being about 40 percent. 150mg of Diazinone per sheet were dissolved in acetone and coated on the exposed surface of each sheet and dried for removal of the solvent. 1g of yeast extract and 4g of sugar were dissolved in fresh water and impregnated in a sheetshaped rubber sponge mass.

This core sheet was assembled with the said two perforated and coated sheets substantially in a similar way as shown on the drawing and the thus prepared device was used for catching and killing house flies in a house.

EXAMPLE 3

Two PVC-sheets, each being 9cm × 9cm × 0.5mm, were punched with 27 elongated rectangular evenly distributed openings, each being of 25mm × 5mm, the ratio or percentage of opened area amounting to about 41.6 percent, and were coated with a solution of Phenitrotion, 200g per sheet, in acetone, and dried to remove the solvent.

A mixture of 8g of soya bean powder, 1g of sugar and 5g of millet jelly was extended over a recessed area : 8cm × 8cm × 1.5mm depth, on a hard paper board, of about 3.5mm thickness. Then, the perforated and coated sheet was placed on the above treated, recessed area for unification into a mass. The thus formed device was used for catching and killing cockroaches in a kitchen, living room and the like.

EXAMPLE 4

A PVC-resin sheet, 0.3mm thick, was glued together with a pervious and absorbing rubber sponge sheet, 0.5mm thick, having an effective area of 16cm × 6cm. The thus assembled sheet was punched out with 42 elongated perforations with rounded ends, each perforation being of 24mm length and 6mm width. These perforations were well distributed and arranged geometrically, to provide a ratio or percentage of open area amounting to about 54 percent.

Then, the sponge sheet portion was impregnated with a solution of 150mg of DDVP per sheet. These perforated and impregnated sheet assemblies were further assembled together with a filter paper impregnated with 2g of dried waste from a wine evaporation step and 5g of sugar dissolved in fresh water. The final assembly was carried out substantially in the same manner as shown on the drawing. This finally assembled device was used for catching and killing flies in a living room, dining room or the like.

INSECTICIDAL EXPERIMENT 1

A cubic chamber, of 2m × 2m × 2m, having a volume of 8m$^3$, was prepared by a wooden framework. Two opposing sides of this chamber were covered with lawn or cheese cloth sheets, while the two remaining sides and the ceiling of said chamber were covered with transparent vinyl film sheets. This small chamber was placed on a floor of a building, so as to provide an experimental vessel. The testing device was of the same structure as was referred to in the foregoing Example 1, but the overall dimensions were reduced to one third of those described therein. As a comparison control, filter paper of one third size was used. This paper was impregnated at first with sugar solution, the rate of sugar used being the same as before. 150 living female and male house flies were introduced into the testing vessel and mortality rates were observed with lapse of time.

During the experiment, glass-made dishes, each containing a mass of sanitary cotton impregnated with sugar solution, were placed on the floor. The experimental vessel was artificially lighted to ensure evenness of the lighting. The experimental results were as follows:

|  | elapsed days | \multicolumn{6}{c}{elapsed hours and resulting mortality rate, %} |  |  |  |  |  |
|---|---|---|---|---|---|---|---|
|  |  | 1 | 2 | 3 | 4 | 5 | 24 |
| test with | 1 | 18.0 | 33.3 | 40.7 | 49.3 | 58.7 | 86.0 |
| inventive | 7 | 11.3 | 29.3 | 37.3 | 45.3 | 54.7 | 79.3 |
| device of | 14 | 24.0 | 48.7 | 49.3 | 53.3 | 61.3 | 97.3 |
| ⅓ size | 30 | 12.0 | 28.0 | 35.3 | 48.7 | 55.3 | 84.7 |
| test with | 1 | 20.0 | 33.3 | 41.3 | 53.3 | 59.3 | 87.3 |
| comparison | 7 | 16.7 | 31.3 | 43.3 | 56.7 | 61.0 | 80.7 |
| control | 14 | 12.7 | 18.7 | 23.3 | 28.0 | 31.3 | 46.0 |
|  | 30 | 3.3 | 6.7 | 10.7 | 12.0 | 15.3 | 18.7 |

As may be seen clearly from the experimental results above tabulated, the mortality percentages do not show much appreciable difference in the killing effects between the two cases, in the initial stages of the comparative experiment. However, it should be remarkably noted that the device of the present invention shows a substantial superiority in residual effective power over the conventional combined simultaneous use of te insect-attracting agent with the insecticide. Therefore, it can be definitely said that for obtaining a long time-extended durable effect, the device of the present invention can be used with remarkable results.

Test of Stability 1

When the influence on the stability of the effectiveness was tested, the following results were observed between the present invention and the prior art.

COMPARATIVELY TESTED DEVICES

A. Inventive

Each of two plastic sheets, 8cm × 3cm, was punched with a number of round holes of 5mm diameter, so as to represent a ratio or percentage of open area of 32.5 percent. The exposed surfaces of these perforated sheets were coated with a solution of 25mg of CAVP in acetone. The, 0.5g of meat extract and 2.0g of sugar were dissolved in water. Filter paper was impregnated with this solution, and dried. Using this filter paper as the core sheet, the perforated sheets were assembled together, substantially in a similar manner as was described with reference to the drawing, so as to provide a device in accordance with the present invention.

B. Conventional 0.5g of meat extract and 2g of sugar were dissolved in water and used to impregnate filter paper of 8cm × 3cm, which was then dried. Then 25mg of CAVP were dissolved in acetone and the solution was coated on one surface of the said filter paper which was then dried, so as to provide a conventional and comparative device.

2. TESTING METHOD

The said device "A" and "B" were positioned in an auxiliary holding frame which was then introduced into an envelope. The effective substance in both cases was held out of contact with the envelope. These sealed-in devices were preserved in a constant temperature vessel kept at 50°C and measured at varying time intervals so as to determine the respective CAVP-contents.

3. METHOD OF ANALYSIS

Inventive device A was tested for its CAVP-content by acetone extraction from the perforated plastic sheets. In the case of the conventional device B, the filter paper was cut into small pieces and the contained CAVP was extracted with acetone. Then, using diphenyl as a marker, the quantity of CAVP was determined by gas chromotography.

4. TEST RESULTS

| Number of elapsed days | Percentage of Residual Insecticide upon completion of Stability Test at 50°C | |
|---|---|---|
|  | Inventive Device "A" | Conventional Device "B" |
| starting day | 100 | 100 |
| 1 | 98.6 | 81.4 |
| 4 | 94.8 | 35.4 |
| 7 | 91.0 | 15.0 |
| 10 | 88.2 | 6.8 |
| 14 | 85.6 | 0 |
| 21 | 81.2 | 0 |
| 30 | 74.8 | 0 |

As may be clearly seen from the foregoing test results, the separated positioning of the insecticide from the insect-attracting agent serves highly effectively for the improvement of the stability of the insecticide.

INSECTICIDAL EXPERIMENT 2

In our experimental laboratory, a small glass experimental space of 1.8m × 1.8cm × 10cm was provided. Each of the inside surface of these glass plates was coated with a thin layer of a mixture of liquid paraffin and white vaseline, so as to prevent cockroaches from escaping.

Testing devices, inventive and conventional, were prepared as in the foregoing example 3.

Two shelters were placed on the floor of said space at opposite corners, while, at one of the remaining corners there was placed a round glass dish of 9cm-diameter with a height of 2cm and including a mass of cotton impregnated with aqueous sugar solution. At the final corner, the testing devices were positioned.

One day before initiation of the experiment, 50 of each male and female cockroaches were introduced into the experimental space for advance domestication.

Then, the experimental test was started and after a lapse of 48 hours, the mortality rate was determined. The experimental space was artifically illuminated as before and daily from 9.00 A.M. to 9.00 P.M.

The results are shown below:

| Number of days after breakage of the sealed envelope | Mortality (%) after 48 hrs. | | | | |
|---|---|---|---|---|---|
| | after one day | after seven days | after 14 days | after 30 days | after 60 days |
| Inventive (3) | 74 | 81 | 68 | 72 | 78 |
| Comparison control (4) | 81 | 78 | 69 | 42 | 17 |

As seen from the above results, the effectiveness is substantially similar upon lapse of one day, while, with progress of the successive days, the mortality rates showed substantial differences between the inventive (3) and the conventional (4) devices, thereby demonstrating a substantially superior residual effect in the invention over the comparative conventional case.

TEST ON STABILITY 2

1. Tested Devices:
   A' ... Inventive devices according to Examples 2, 3 and 4;
   B' ... Conventional comparative devices according to these Examples;

2. Method of Test:
   Similar to before.

3. Method of Analysis:
   Similar to before.

4. Test Results Results:

| Number of elapsed days | Percentage of Residual Insecticide upon completion of Stability Test at 50°C | | | | | |
|---|---|---|---|---|---|---|
| | Example 2 | | Example 3 | | Example 4 | |
| | Sample Device A' | Sample Device B' | Sample Device A' | Sample Device B' | Sample Device A' | Sample Device B' |
| starting day | 100 | 100 | 100 | 100 | 100 | 100 |
| after lapse of 1-day | — | — | — | — | — | 76.1 |
| after lapse of 7-days | 98.7 | 86.4 | 99.2 | 92.0 | 85.1 | 3.2 |
| after lapse of 14-days | 98.0 | 80.2 | 98.5 | 85.5 | 73.7 | 0 |
| after lapse of 30-days | 95.8 | 69.6 | 97.3 | 76.4 | 55.2 | 0 |
| after lapse of 60-days | 92.3 | 60.1 | 94.6 | 71.2 | 38.9 | 0 |

The embodiments of the invention in which an exclusive property or privelege is claimed are defined as follows:

1. In an insecticide and insect attractant carrier structure positioning each independently and thereby stabilizing the residual effectiveness of insecticides adversely affected by the presence of insect attractants, the improvement comprising a base sheet affixed to at least one perforated sheet, having a number of perforations, and having about 25–70 percent perforated area, each perforation having sufficient width to accomodate insects attracted to effective insect attractant adhered, impregnated, or coated, without insecticide, to said base sheet, with effective contact insecticide adhered, impregnated, or coated, without insect attractant, to said perforated sheet, said insecticide, thereby independently positioned from said insect attractant, being stabilized against and free from decomposition, instability, loss of residual effectiveness and other adverse effects attributable to contact with insect attractant.

* * * * *